(12) United States Patent
Santos et al.

(10) Patent No.: US 9,198,973 B2
(45) Date of Patent: Dec. 1, 2015

(54) PAMAM, SPACER MOLECULE AND CAFESTOL POLYMERS

(71) Applicants: Fundación Fraunhofer Chile Research, Las Condes, Santiago (CL); Universidad de Talca, Talca (CL)

(72) Inventors: Leonardo S. Santos, Talca (CL); John Amalraj, Talca (CL); Esteban F. Duran Lara, Talca (CL); Fabiane M. Nachtigall, Talca (CL)

(73) Assignees: Fundacion Fraunhofer Chile Research (CL); Universidad de Talca (CL)

( * ) Notice: Subject to any disclaimer, the term of this patent is extended or adjusted under 35 U.S.C. 154(b) by 62 days.

(21) Appl. No.: 13/919,403

(22) Filed: Jun. 17, 2013

(65) Prior Publication Data

US 2014/0371401 A1 Dec. 18, 2014

(51) Int. Cl.
| | |
|---|---|
| A61K 47/00 | (2006.01) |
| C08L 77/00 | (2006.01) |
| C08L 79/00 | (2006.01) |
| A61K 47/48 | (2006.01) |
| C08L 79/02 | (2006.01) |

(52) U.S. Cl.
CPC ........... *A61K 47/48207* (2013.01); *C08L 79/02* (2013.01); *C08L 2203/02* (2013.01)

(58) Field of Classification Search
None
See application file for complete search history.

(56) References Cited

U.S. PATENT DOCUMENTS

| | | | |
|---|---|---|---|
| 8,252,834 B2 | 8/2012 | Baker et al. | |
| 8,313,778 B2 | 11/2012 | Seiler et al. | |
| 2010/0028402 A1 | 2/2010 | Dobrovolskaia et al. | |
| 2010/0158850 A1 | 6/2010 | Baker, Jr. et al. | |
| 2012/0277158 A1* | 11/2012 | Castaigne et al. | 514/17.5 |
| 2013/0136697 A1 | 5/2013 | Kannan et al. | |

FOREIGN PATENT DOCUMENTS

| | | |
|---|---|---|
| WO | WO 2010/054321 | 5/2010 |
| WO | WO 2010/147831 | 12/2010 |
| WO | WO 2011/123591 | 10/2011 |

OTHER PUBLICATIONS

Geraldo et al. "Supramolecular complexes of quantum dots and polyamidoamine (PAMAM)-folate derivative for molecular imaging of cancer cells." *Anal Bioanal Chem.* vol. 400. 2011. pp. 483-492.
Kim et al. "PAMAM-PEG-PAMAM: Novel Triblock Copolymer as a Biocompatible and Efficient Gene Delivery Carrier" *Biomacromolecules.* vol. 5. 2004. pp. 2487-2492.
Scharnhop et al. "Isolation of coffee diterpenes by means of high-speed countercurrent chromatography." *J. of Food Composition and Analysis.* vol. 22. 2009. pp. 233-237.
Yoo et al. "Biodegradable Nanoparticls Containing Doxorubicin-PLGA Conjugate for Sustained Release." *Pharmaceutical Research.* vol. 16. No. 7. 1999. pp. 1114-1118.
Duran et al. "Nanocomposites PAMAM derivatives with antitrombogenic activity and hemocompatibility." *TechConnect World Summit & Innovation Showcase.* 2012. Abstract only.
Lee et al, "Natural diterpenes from coffee, cafestol and kahweol induce apoptosis through regulation of specificity protein 1 expression in human malignant pleural mesothelioma." *Journal of Biomedical Science* 19(60):1-10 (2012).
International Search Report for PCT/IB2014/063010 (mailed Dec. 24, 2014).
International Written Opinion for PCT/IB2014/063010 (mailed Dec. 24, 2014).

* cited by examiner

*Primary Examiner* — Ana Woodward
(74) *Attorney, Agent, or Firm* — Merchant & Gould P.C.

(57) ABSTRACT

The present invention is directed to a polymeric compound with a size in a nanometric scale, useful as a biocompatible carrier for the transport and delivery of active agents into a fish, insect, animal, reptile, bird, human, or plant, wherein said polymeric compound comprises PAMAM (polyamidoamine) dendrimers, a spacer molecule, and cafestol, wherein the polymeric compound of the invention comprises a structure of the kind (cafestol-PAMAM derivative)$_2$-spacer molecule. Use of the compound as a biocompatible carrier for transport and delivery of antithrombotic active agents is disclosed. Procedures for obtaining a polymeric compound comprising the activation of cafestol, activation of polyethylene glycol, and formation of cafestol-PAMAM-PEG-PAMAM-cafestol are also disclosed.

12 Claims, 2 Drawing Sheets

PAMAM, SPACER MOLECULE AND CAFESTOL POLYMERS

BACKGROUND

Currently, there are many human diseases—such as inflammatory pathologies, autoimmune diseases, or acute pain—which have to be endured by people, which require development of new technologies to advance diagnosis or accelerate and improve therapeutic procedures which can overcome or at least alleviate a disease.

In spite of recent advances in biotechnology and current medicine associated to prevention, early diagnosis, and therapeutic treatments, there are still many challenges to improve the early diagnosis and the life quality related to therapies. Without going too far, and as an example, cancer is still a high mortality index disease which only in the United States takes more than 500,000 lives per year.

Given the need to improve the diagnostic and therapeutic systems, including the enormous advances that modern medicine has made, the development of new materials and their combination has been favored, allowing the transport and delivery of specific molecules, either probes in case of need of a diagnosis, or therapeutic compounds or drugs, proteins or nucleic acids, acting in very precise locations inside the animal or human body which is in need thereof.

For example, gene therapy advances considers the transport of isolated molecules of nucleic acids, such as genes and/or small interference RNA molecules (siRNA) to specific cells.

Exogenous siRNA can regulate the expression of genes codifying proteins associated with a particular pathology, as long as they are incorporated directly into the cells where specific gene expression regulation is required. Nevertheless, therapeutic applications of siRNA are precisely restricted due to unsolved problems involving efficient transport and delivery to the specific zone where their action is required: intracellular medium of those specific cells inside a person in need of a therapeutic treatment.

An efficient delivery of siRNA therefore requires improving incorporation thereof inside the cells to be treated, and previously, avoiding its degradation in blood and extracellular medium. Precisely, the present invention shows an improved alternative for transport and delivery of molecules, such as siRNA, using a new transport polymeric structure constituted by PAMAM (polyamidoamine) dendrimers, a spacer molecule, and cafestol.

Great part of the advances in the development of new transport and delivery materials for use with biocompatible active substances in the treatment of animals and humans in particular, are associated with the design of new compositions investigated in the field of nanotechnology, which are also useful as carrier vehicles for probing molecules or molecules with a therapeutic end, and which are able to recognize, with a high precision degree, target cells to which their valuable material of last generation molecules with biomedical activity, either diagnostic or therapeutic.

As previously mentioned, one of the advantages that must be assured in the development of new transport and delivery carriers for support substances in medical treatments, is that the carrier is conformed in base of polymers which can bind active molecules and transport them to a predetermined location. These polymers must have innocuous features, at systemic level as well as in a particular organ, tissue, or target cells where it is expected that the diagnostic or medical molecule is delivered, avoiding degradation of the transported molecule, and therefore assuring efficient distribution to the targeted location, mainly at intracellular level.

Thus, it is important to take into account that the polymeric structure of these vehicles or carriers must be characterized by showing a solubility compatible with the fluids with which will interact until arriving to its destination, in such a manner to improve its stability—and the transported molecule—during the journey and favoring delivery times to the target site of said active molecule to be distributed, especially when the latter shows a low solubility degree, that prevents arriving by itself to the place where its action is expected to occur.

In this way, the carrier materials must comply with the need of avoiding fast or systematic degradation of themselves as well as the transported molecule and during all the journey to the targeted site. It is also expected that once the active substance is delivered, the carrier polymers should be degraded or eliminated from the patient's body, as long as the whole process does not produce co-lateral damages.

All of the above can be summarized in that a good active molecule, with a biomedical utility, carrier system must favor arrival and accumulation of an intact active substance, either at organ level, in a tissue or to targeted cells. Among the last generation carriers which have been developed for in vivo transport of drugs, proteins or isolated nucleic acids, we can find polymeric micelles, hydrogels, liposomes, or water-soluble conjugated polymers, developed in great part by application laboratories in the field of nanotechnology.

As such, nanotechnology associated to medicine, is born through convergence and complementarity of scientific findings obtained from research in physical, chemical, and biological sciences, being considered nowadays as one of the most promising technologies in the field of human and animal health in general (*Ann. Bioanal. Chem.*: 400: 483-492). Among the technological advances made in the field of nanotechnology reported during the last five years, different polymeric approaches have been reported, related to structures in the scale between 1 and 100 nanometers (1-100 nm). Among the advances in nanotechnological structures platforms, we can consider four of them as widely acknowledged by favoring production of relatively precise nano-structures, such as fullerenes, nanotubes, quantum dots, and dendrimers.

A family of potential carriers for drug and/or gene delivery are dendrimers, which are polymers (macromolecules between 5,000 and 500,000 g/mol), mono-disperse, spherically shaped, well defined and regularly branched, and which can be easily modified or "activated" in their surfaces with functional moieties such as amines ($-NH_2$), carboxylates ($-COOH$), etc., which allow coupling to said modified dendrimers of biomedical important substances which need to be transported and delivered to very specific locations (organs, tissues, or specific cells) inside an animal or a person.

Dendrimers are therefore, potential polymeric structures which can be used as carrier vehicles for the administration of either drugs, proteins, or isolated nucleic acids, associated to therapeutic procedures wherein the administration to a patient of active substances to be distributed to preferred tissues, at a controlled or preferred delivery rate, and protected from metabolic degradation before arrival to their final destination where its action is required, is needed. Also, the relatively empty intra-molecular cavity that dendrimers have, would facilitate the "molecule hosting", providing new opportunities for further designs of delivery of drugs and genes.

Structurally, dendrimers are a class of macromolecules at a nanometric scale (less than 1/1,000,000 meters), and therefore they are also known as nanostructures, having multivalent surfaces allowing further modification with functional moieties (—NH₂, —COOH, alkyl, etc.), facilitating later the binding of probing molecules for diagnosis or molecular agents for the treatment of diseases.

The chemical versatility of dendrimers has produced its intense research in the last years, due to its potential use in biomedical applications such as gene therapy, in vivo drug or therapeutic molecules or diagnosis probes delivery.

These nano-structures (dendrimers) have the versatility to allow conjugation at surface level of their polymeric structure, with different functional moieties useful in modern molecular medicine (probes, nucleic acids, proteins or medicinal drugs). Nevertheless, conjugation of said functional moieties to the dendrimer depends on the reactivity of the peripheral groups present in the dendrimer. Therefore, there is also the need to broaden the range of functional moieties that can be present in the surface of the dendrimer, and thus, increasing the possibility of conjugation of different and new alternative probe molecules or medicinal drugs, to the surface of the dendrimer, and which can be delivered to a target organ, tissue, cell, for those active substances.

Since the utility of dendrimers is widely recognized as a modern tool for transport of other active molecular agents, many types of dendrimers have been developed and employed in many applications including medicine, chemistry, and pharmacy.

This has produced the development of hundreds of polymeric drug and therapeutic molecular agents carriers, in many laboratories worldwide, being the ones based in PAMAM (PolyAMidoAMine) well-known as highly efficient in the transport and delivery of genes, as efficient as those based in polyethylenimine (PEI), recognized for being the most efficient carriers known nowadays.

Literature teaches many different approaches for preparing dendrimers which are functionalized for recognizing determined cell types, through conjugation with ligands that can interact with target molecules in specific tissues and/or defined cells (for example, through recognition and binding to surface membrane receptors of said target cells). Some background shown in the literature regarding conjugated polymers with potential application in biomedicine is mentioned here below.

Patent application WO2011053618 teaches new procedures for the synthesis of dendrimers based in PAMAM modified in its ends with multiple hydroxyl groups or ethylenglycol oligos, which are compatible with further conjugation with functional ligands such as therapeutic agents, drugs, probes, etc.

PAMAM dendrimers have been used widely in the design of new hydrogels formed as small cross-linked particles in a size ranging from 25 nm a 10 μm (10,000 nm) which are appropriate according to the inventors (check international patent application WO2011123591) for distributing hydrogel through any orifice, tissue, muscle route, subcutaneous or ocular way of the body of a patient in treatment or under observation for diagnosis. In the hydrogels of WO2011123591, PAMAM dendrimers are cross-linked with asymmetrical terminal groups in such a manner that a terminal group is directly involved in the formation of the hydrogel and the other is enabled to conjugate—and thus bind and transport—therapeutic or diagnostic molecules which are to be distributed with the hydrogel.

Among the applications in medicine which have been published using dendrimers, the use of PAMAM for treating inflammatory disorders, and those of autoimmune nature, such as rheumatoid arthritis, osteoarthritis, juvenile idiopathic arthritis, psoriasis, lupus erythematosus, Crohn's disease, or sarcoidosis, and where PAMAM dendrimers are used for the transport of therapeutic agents, for recognition or diagnosis associated to the mentioned diseases has been considered (check international patent application WO2010054321).

Patent application US2010158850 describes coupling of two dendrimers, preferentially PAMAM and POPAM (PolyPropylAMine) and wherein each of the coupled dendrimers is modified by functional groups allowing further conjugation with therapeutic agents, diagnostic therapeutic pre-treatment or for evaluation of results of a given therapy, for example against cancer, through direct recognition of surface receptors in target cells by these polymeric structures coupled with selected therapeutic or diagnostic agents.

Patent application WO2010147831 describes as a carrier for active agents, a composition comprising N-acetyl cysteine bound to PAMAM dendrimer, and wherein the latter also binds to the active agent to be transported, through disulfide bonds.

Notwithstanding the foregoing, the use of PAMAM as structural base in the development of carriers and delivery agents in situ and in vivo for genes, therapeutic drugs, or diagnostic probes, presents some problems which are to be solved and which are associated mainly to a low solubility of these dendrimers in water, as well as certain toxicity and low capacity in penetrating the cell membrane. This has led to research modifications to this PAMAM dendrimers, binding them to other polymers such as polyethylene glycol (PEG), since the latter shows very low immunogenicity, is biocompatible and presents high solubility in water (Kim et al (2004), *Biomacromolecules* 5: 2487-2492).

Among the polymers developed for improving the in vivo efficiency of these carriers for genes, therapeutic drugs and/or diagnostic probes, and combining the properties of PAMAM and PEG, the work of Kim et at (*Biomacromolecules* 5: 2487-2492, 2004) can be mentioned. They developed a hybrid, self-assembling co-polymer, and based in the order of a polymeric structure of three blocks: PAMAM-PEG-PAMAM. Said structure shows an advance over water solubility compared to polymers based exclusively in PAMAM, but still has cytotoxicity and transfection problems. Therefore, this cannot be referred as an improved carrier, and thus, it is not fit for use in biomedical treatments.

As summarized, notwithstanding the broad impulse currently given worldwide to the development of new generations of in vivo carrier polymers for medical support substances in therapy or diagnosis, the need of developing new polymeric preparations, which are not only biocompatible, with a good cellular permeability, and not toxic to the treated organism, but also showing higher versatility for coupling new generations of therapeutic or diagnostic substances still to be developed which will require precise transportation to a specific target in a patient in need thereof, still exists.

SUMMARY

The present invention is related to new biocompatible polymer conjugates forming stable structure, of nanometric size which are useful as carrier and delivery vehicles, in fishes, insects, animals, reptiles, birds, human body, plants, or microorganisms, of substances such as different compounds, drugs, proteins, or isolated nucleic acid sequences (genes, siRNA, etc.) in directed treatment of organs, tissues, or specific cell types which require or it would be desired to apply said compounds, drugs, proteins, or isolated nucleic acid sequences to. The new carriers shown in the present invention also allow delivery inside a fishes, insects, animals, reptiles, birds, human body, plants, or individual cells in the need thereof, of probing molecules, allowing timely and precise diagnostic of different fish, insect, animal, reptile, bird, human, or plant pathologies. Furthermore, the invention also allows delivering inside a fish, insect, animal, reptile, bird, human, or plant different compounds, drugs, or nucleic acid sequences with a therapeutic or medical end.

The polymeric carriers of the present invention comprise PAMAM (polyamidoamine), a spacer molecule and cafestol (a diterpene derived from coffee) conjugates, wherein the polymeric structure grants an increased cell permeability, improving its performance as carrier and delivery vehicles, such as for example in intracellular delivery of isolated deoxyribonucleic acid (DNA) or ribonucleic acid (RNA) sequences, as well as therapeutic drugs, proteins and/or diagnostic probes.

DETAILED DESCRIPTION

Figure 1:
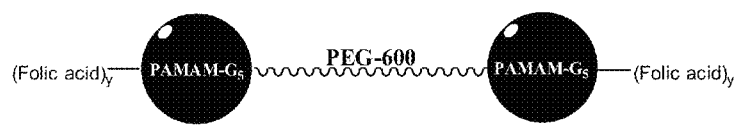
FIG. 1, shows a schematic representation of the structure of a dendrimer PAMAM-PEG-Folic acid.

The need for new biocompatible, nanometric sized, and useful as improved carriers of substances for intracellular delivery in different organisms or at single cell level, of relevance in different applications, such as for example therapy or diagnosis, polymeric substances or combinations thereof, has driven the researchers of the present invention to develop new polymeric vehicles combining the known advantages of dendrimers, such as PAMAM; in association with a spacer molecule, such as polyethylene glycol, polyethylene oxide, polyethylene, polypropylene polyurethane; with cafestol. In this way, the present invention is directed to a polymeric compound which size is in nanometric scale, useful as a biocompatible carrier for the transport and delivery of active medicinal agents, allowing diagnosis or treatment in a fish, insect, animal, reptile, bird, human, or plant in need thereof, wherein said polymeric compound comprises PAMAM (polyamidoamine) dendrimers, a spacer molecule such as polyethylene glycol, polyethylene oxide, polyethylene, polypropylene polyurethane, and cafestol.

Although the disclosure is directed in part to particular human diseases, the scope of the invention and the use of the disclosed polymeric carriers is broader and must be understood as a general delivery or carrier molecule for the transport of molecules, compounds, drugs, nucleic acids, proteins, peptides, or other compounds of interest, to different organisms, such as fishes, insects, animals, reptiles, birds, human body, plants, or microorganisms.

The polymeric compound of the invention comprises a structure of the kind (cafestol PAMAM derivative)$_2$-spacer molecule. In a particular embodiment, the structure is (cafestol PAMAM derivative)$_2$-PEG, which exhibits—compared to other nanostructures based in PAMAM—an improved cellular permeability and thus, a higher capacity for the delivery of the transported substances.

The polymeric compound of the present invention can also comprise folic acid in the abovementioned structure (cafestol-PAMAM derivative)$_2$-spacer molecule, or in a particular embodiment (cafestol PAMAM derivative)$_2$-PEG.

The polymeric compound described herein, also has shown an improved protection level before metabolic degradation of drugs or RNA as well as proteins coupled to the novel structure (cafestol-PAMAM derivative)$_2$-spacer molecule, or in a particular embodiment (cafestol PAMAM derivative)$_2$-PEG, which represent important technical advances in regard of prior art, and which is described in detail here below.

The need for better carrier vehicles for medically important substances has motivated the authors of this invention to look for new polymeric compositions allowing to improve the functional features of PAMAM and a spacer molecule couplings, wherein said molecule is selected for being a neutral molecule, soluble in water, and with a wide variety of uses in biomedicine, as well as biotechnological applications. The spacer molecule should also have high biocompatibility and scarce immunogenicity. For example, and without the intention of limiting the scope of the invention, the spacer molecule can be, among others, PEG, which has been recognized and approved by the FDA (Food and Drug Administration, USA) as a safe molecule for medical treatments.

The authors of the present invention, have found that the properties as polymeric medicinal carrier and delivery agent of the associations between PAMAM and a spacer molecule, more specifically PEG, improve substantially when incorporating cafestol, which is a natural substance, from the diterpene family and it is found in coffee in concentrations between 0.25 to 0.55 per gram of total coffee.

Figure 4:
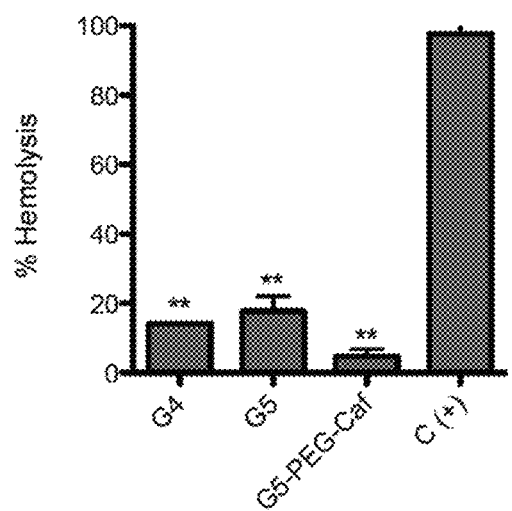
FIG. 4, shows erythrocytic hemocompatibility of PAMAM G4, PAMAM G5, and PAMAM-PEG-CAFESTOL.

The present invention combines conjugation of cafestol to a structure having PAMAM bound to a spacer molecule, and wherein the final structure obtained shows an improved permeability level in different membranes from different human cell types, thus improving the intracellular delivery of various active substances, such as anti-cancer drugs, interference RNA, proteins, and peptides. Added to that, the nanocarrier, according to studies performed by the inventors, would have a great compatibility with cellular membranes, which could be penetrated without altering their integrity (FIG. 4).

Figure 2:
FIG. 2, shows a schematic representation of the structure of a dendrimer PAMAM-PEG-Cafestol of one embodiment of the present invention.

A preferred embodiment of the present invention is related to the preparation of new dendrimer carrier materials, having two arms of PAMAM dendrimers bound by a spacer (FIG. 1, where a particular exemplification of the invention is shown, wherein the spacer molecule is PEG), and wherein the PAMAM periphery is modified with folic acid and cafestol (FIG. 2). The new polymeric structure provided by the present invention is a promising candidate for biomedical applications such as in vivo delivery of drugs, proteins, and nucleic acids sequences. It has been shown previously that Generation 4 PAMAM conjugated with amino acids, such as arginine, are good nanocarriers, but the new polymer described in the present invention, would have higher permeability properties, due to the presence of cafestol and optionally folate, increasing therefore the bioavailability and decreasing the delivery time and further nanoclearance of the polymer. Specifically, folate is an important cofactor for the synthesis of nucleotides (which is performed in the cell nucleus), and thus, would increase the directionality of release of genes towards the nucleus.

The dendrimers of the present invention correspond to a polymeric nucleus which can further comprise for example triacrylate, tetraacrylate, triepoxide, tetraepoxide, diglycidyl, aminoethanol aniline, ethylendiamine, triphenylmethane, triglycidylether, bis(glycidoxyphenyl)methane, methyl bis (diglycilaniline), tetraepisulphur and tris(glycidoxyphenyl) methane. The number of dendrimer materials can be from 1 to 6.

The spacer molecule is selected among polyethylene glycol (PEG), polyethylene oxide, polytheylene, polypropylene polyurethane. The preferred spacer for the present invention is polyethylene glycol (PEG).

The molecular weight of the polymeric compound of the present invention is in the range from 200 to 10,000 g/mol.

The polymeric compounds of the present invention can further comprise folic acid in the core or in the periphery of the dendrimer.

In a particular embodiment of the present invention, the structure cafestol-PAMAM-PEG-PAMAM-cafestol (FIG. 2), shows higher cellular permeability, thus favoring a higher bioavailability of siRNA, genes, and therapeutic or diagnosis drugs.

The new carriers described in the present invention have incorporated the addition of cafestol for conjugation with PAMAM and a spacer molecule, and wherein initially, PAMAM (generations 0 to 5) are cross-linked with nucleus of the spacer molecule. In the present invention, various PAMAM derivatives are used (including surface modifications of PAMAM with functional groups such as alkyl, folic acid, furanylamine, among others) to which cafestol is later coupled (FIG. 2). The presence of a spacer molecule, preferably PEG, in the new carriers of the invention, is used as a spacer agent in the nanostructure (cafestol-PAMAM derivative)$_2$-PEG, as can be seen in particular embodiments of the invention in FIGS. 1 and 2.

The present invention also comprises a procedure for obtaining the carrier molecules of the invention, for a particular embodiment wherein the spacer molecule is PEG, of the polymer PAMAM (polyamidoamine), PEG (polyethylene glycol), and cafestol, comprising activation of cafestol, activation of polyethylene glycol, and formation of cafestol-PAMAM-PEG-PAMAM-cafestol. Wherein said procedure comprises preparing PAMAM-folic acid, then reacting the activated polyethylene glycol to form PAMAM-folic acid-PEG-PAMAM-folic acid and then reacting cafestol to form the polymer cafestol-PAMAM-PEG-PAMAM-cafestol.

The procedure for obtaining the polymer of the invention PAMAM (polyamidoamine), PEG, and cafestol can also comprise preparing PAMAM-folic acid; adding polyethylene glycol previously activated with p-nitrophenyl chloroformate and pyrimidine in dichloromethane, to form PAMAM-folic acid-PEG-PAMAM-folic acid; the PAMAM-folic acid-PEG-PAMAM-folic acid is dissolved in DMSO and a mixture of cafestol is added, which was previously activated with p-nitrophenyl chloroformate and pyrimidine in dichloromethane, and 4-dimethylaminopyridine dissolved in DMSO to form the polymer cafestol-PAMAM-PEG-PAMAM-cafestol under a N$_2$ atmosphere.

Further below are described procedures exemplifying obtaining and use of the polymeric carriers, considering a specific embodiment of the present invention, for (cafestol-PAMAM derivatives)$_2$-PEG, allowing reproducibility thereof, without limiting the scope in biomedicine of these new polymeric conjugates.

EXAMPLES

The following examples describe, step by step, the procedure for obtaining a particular embodiment of the present invention considering the structure cafestol-PAMAM-PEG-PAMAM-cafestol, described in FIG. 2.

1.1.—Isolation and Purification of Cafestol from Coffee

Due to the low solubility of cafestol, this diterpene was extracted from arabic powdered coffee using previously described procedures (Heike Scharnhop, Peter Winterhalter, Journal of Food Composition and Analysis 22, 2009, 233-237) using a Soxhlet extractor, and according to the following steps:
(i) 50 g of powdered coffee were extracted with n-hexane in a Soxhlet extractor during 16 hours.
(ii) the solvent was removed under reduced pressure until obtaining a viscous oil from coffee
(iii) the oil from the coffee was saponified with 200 ml of a ethanolic potassium hydroxide (10%) at 90° C. during 4 hours,
(iv) ethanol was evaporated and the residue was dissolved in 200 deionized water and 25 ml of sodium chloride solution (10%) at 70° C. for 1 hour,
(v) the solution obtained was extracted with diethyl ether (3×50 ml) and the organic layer was washed with a solution of 2% sodium chloride, dried over anhydrous sodium sulfate and the solvent was removed under low pressure.
(vi) cafestol was isolated using a chromatographic column (silica gel 60-120 mesh) using diethyl ether and chloroform as solvent.

The extraction procedure allows a high recovery yield (90% with respect to the expected mass in coffee).

1.2.—Activation of Cafestol

Cafestol was activated with p-nitrophenylchloroformate using a procedure previously described (H-S. Yoo, J-E. Oh, K-H. Lee, T-G. Park, *Pharmaceutical Research* 16: 1999, 1114-1118):
(i) Cafestol (10 mg) and p-nitrophenylchloroformate (17.9 mg) were dissolved in 1.5 ml of dichloromethane and cooled down at 0° C.
(ii) 12 mg pyridine were dissolved in 1.5 ml of dichloromethane and added to the cafestol solution
(iii) the reacting mass was kept under constant agitation during 12 hours at room conditions, and afterwards it was washed with 0.1% HCl and brine solution,
(iv) the dichloromethane layer was dried over anhydrous Na$_2$SO$_4$ and the solvent was removed under distillation under low pressure.

Figure 3:
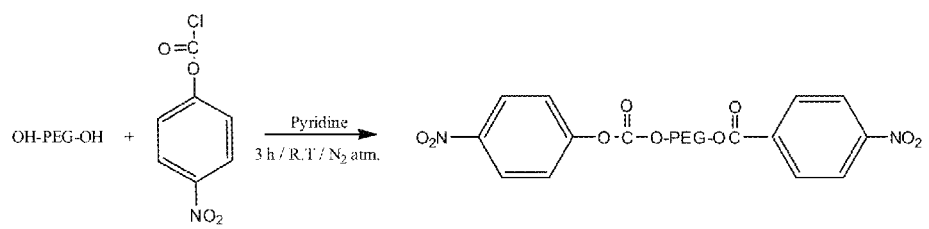
FIG. 3, shows a chemical equation representing the activation of polyethylene glycol (PEG).

1.3.—Activation of Polyethylene Glycol (PEG)-600 (FIG. 3)
(i) 200 mg of PEG-600 y p-nitrophenylchloroformate (403 mg) were dissolved in 10 ml 10 ml of dichloromethane (DMC) and cooled at 0° C.,
(ii) 263 mg of pyridine were added to the reaction mix and were kept under constant agitation for 3 hours, at room conditions,
(iii) after 3 hours, the reaction is diluted with 10 ml dichloromethane and is washed with 0.1% HCl and brine solution,
(iv) the dichloromethane layer was dried over anhydrous Na2SO4 and the solvent was removed using distillation,
(v) the PEG derivative is recrystallized in diethyl ether.

1.4.—Preparation of PAMAM-G$_5$-Folic Acid

PAMAM-G$_5$-folic acid was prepared using a modified procedure (*Anal. Bioanal. Chem.* 2011, 400, 483-492).
(i) 5 mg of folic acid and 200 mg of dicyclohexylcarbodiimide were dissolved in a mixture of dimethyl sulfoxide (1 ml) and dimethyl formamide (2.7 ml) under a N$_2$ atmosphere.
(ii) PAMAM-G$_5$ was dissolved in 10 ml deionized water and then added to the mixture of folic acid
(iii) the reaction mixture was kept under constant stirring during 3 hours, at room temperature and under N$_2$ atmosphere.
(iv) the reaction mixture was dialyzed in a cellulose dialysis bag (molecular cut size: 500 Da) against deionized water during 24 hours and with the aim to remove free folic acid (unreacted folic acid) as well as other reactants. Finally, the reaction mixture was lyophilized to obtain the desired product.

1.5.—Preparation of PAMAM(G5)-FA-PEG-PAMAM(G5)-FA (FIGS. 1 y 2)
(i) 8 mg of PAMAM(G5)-FA were dissolved in DMSO (2 mL)
(ii) activated PEG-600 (0.15 mg) and 4-dimethylaminopyridine (0.04 mg) were dissolved in 2 ml of DMSO,
(iii) PAMAM(G5)-FA solution was added drop-wise to the PEG-600 solution, at 0° C.,
(iv) the mixture was kept under constant stirring during 72 hours, at room conditions, for further lyophilization, and thus, removal of solvents.

1.6.—Preparation of the Final Structure Useful in the Transport of Active Biomedical Compounds: PEG-PAMAM(G5)$_2$-Cafestol (FIG. 2)
(i) 5 mg of G5-FA-PEG-G5-FA were dissolved in 2 ml of DMSO
(ii) activated cafestol (3 mg) and 4-dimethylaminopyridine (0.76 mg) were dissolved in 2 ml of DMSO,
(iii) the solution of G5-FA-PEG-G5-FA was added drop-wise to the activated cafestol solution at 0° C., under $N_2$ atmosphere.
(iv) the reaction mixture was kept under constant stirring for 72 hours, at room temperature and under $N_2$ atmosphere.

1.7. Evaluation of Hemocompatibility of PEG-PAMAM(G5)$_2$-Cafestol.

Researches further performed tests for evaluating the compatibility of the PEG-PAMAM(G5)$_2$-Cafestol polymer in blood stream as a potential nanocarrier. To this end, the hemolysis and erythrocyte morphology was analyzed. As can be observed in FIG. 4, showing erythrocytic hemocompatibility, through hemoglobin release in the presence of PAMAM G4, PAMAM G5, and PEG-PAMAM(G5)$_2$-cafestol, wherein the positive control (C(+)) is distilled water.

The PEG-PAMAM(G5)$_2$-cafestol polymer of the present invention shows low hemotoxicity, around 4% compared to PAMAM G4 and PAMAM G5, which are above 15% and 20% respectively. In terms of erythrocyte morphology in the presence of the PEG-PAMAM(G5)$_2$-cafestol polymer compound, there are no visible alterations in morphology of erythrocytic membrane, thus, the erythrocytic membrane is not affected by the presence of PEG-PAMAM(G5)$_2$-cafestol. The polymer PEG-PAMAM(G5)$_2$-cafestol also has a significative antithrombotic activity coupled to the lack of cytotoxicity in erythrocytes, therefore, it is an excellent candidate as carrier for antithrombotic drugs and also improving the effect of said drugs.

The invention claimed is:

1. A nanoscale polymeric compound for use as a biocompatible carrier for the transport and delivery of a drug, protein, peptide or nucleic acid in a fish, insect, animal, reptile, bird, human, or plant in need thereof,
wherein the polymeric compound comprises cafestol conjugated with a PAMAM (polyamidoamine) dendrimer, and a spacer molecule, in the following configuration: (cafestol-PAMAM)-spacer molecule-(PAMAM-cafestol);
wherein the spacer molecule is selected from the group consisting of polyethylene glycol (PEG), polyethylene oxide, polyethylene, and polypropylene polyurethane.

2. The polymeric compound according to claim 1, wherein the spacer molecule is PEG.

3. The polymeric compound according to claim 2, wherein the PAMAM dendrimer surface is modified with folic acid.

4. The polymeric compound according to claim 1, wherein PAMAM dendrimer comprises PAMAM G0 to G5.

5. The polymeric compound according to claim 1, wherein PAMAM dendrimer comprises PAMAM G4 to G5.

6. The polymeric compound according to claim 1, wherein the polymeric compound allows transport and delivery of isolated deoxyribonucleic acid (DNA) molecules, isolated gene sequences, isolated ribonucleic acid molecules (RNA), small interference RNA (siRNA), or proteins.

7. The polymeric compound according to claim 1, wherein the drug, protein, peptide or nucleic acid is used as a diagnosis probe for diseases.

8. A biocompatible vehicle for transport and delivery of a drug, protein, peptide or nucleic acid useful in diagnosis or therapy comprising a polymeric compound according to claim 1.

9. A biocompatible vehicle for transport and delivery of an antithrombotic drug, protein, peptide or nucleic acid, comprising the polymeric compound according to claim 1.

10. A process for preparing a polymer comprising PAMAM (polyamidoamine), PEG (polyethylene glycol) and Cafestol, comprising the steps of:
activating cafestol with p-nitrophenylchloroformate, activating PEG with p-nitrophenylchloroformate, and forming Cafestol-PAMAM-PEG-PAMAM-Cafestol.

11. Procedure The process according to claim 10, comprising the step of modifying the PAMAM surface with folic acid to form PAMAM-folic acid, then reacting the PAMAM-folic acid with the activated PEG to form PAMAM-folic acid-PEG-PAMAM-folic acid, and then reacting the PAMAM-folic acid-PEG-PAMAM-folic acid with activated cafestol to form cafestol-(PAMAM-folic acid)-PEG-(PAMAM-folic acid)-cafestol.

12. A process for preparing a polymer comprising PAMAM (polyamidoamine), polyethylene glycol (PEG) and cafestol, comprising the steps of:
modifying the PAMAM surface with folic acid to form PAMAM-folic acid;
activating PEG with p-nitrophenylchloroformate and pyrimidine in dichloromethane;
reacting the PAMAM-folic acid with the activated PEG to form PAMAM-folic acid-PEG-PAMAM-folic acid;
activating cafestol with p-nitrophenylchloroformate and pyrimidine in dichloromethane;
dissolving the PAMAM-folic acid-PEG-PAMAM-folic acid and 4-dimethylaminopyridine in dimethyl sulfoxide (DMSO), and
forming cafestol-(PAMAM-folic acid)-PEG-(PAMAM-folic acid)-cafestol under a $N_2$ atmosphere.

* * * * *